(12) United States Patent
Hall et al.

(10) Patent No.: US 12,004,855 B2
(45) Date of Patent: Jun. 11, 2024

(54) IMPLANTABLE BIOSENSOR

(71) Applicant: The Regents of the University of California, Oakland, CA (US)

(72) Inventors: Drew Hall, La Jolla, CA (US); Saurabh Kulkarni, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/620,337

(22) PCT Filed: Jun. 7, 2018

(86) PCT No.: PCT/US2018/036537
§ 371 (c)(1),
(2) Date: Dec. 6, 2019

(87) PCT Pub. No.: WO2018/227006
PCT Pub. Date: Dec. 13, 2018

(65) Prior Publication Data
US 2020/0196921 A1    Jun. 25, 2020

Related U.S. Application Data

(60) Provisional application No. 62/517,828, filed on Jun. 9, 2017.

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/0031* (2013.01); *A61B 5/05* (2013.01);
(Continued)

(58) Field of Classification Search
CPC ..... A61B 5/14532; A61B 5/0031; A61B 5/05; A61B 5/14539; A61B 5/14865; A61B 5/145; A61B 2560/0219; A61B 2560/0214
See application file for complete search history.

(56) References Cited

U.S. PATENT DOCUMENTS

| 5,198,093 A | 3/1993 | Sydlowski et al. |
| 5,766,432 A * | 6/1998 | Dunn ................. A61B 5/14539 204/406 |

(Continued)

OTHER PUBLICATIONS

Lee, K.H., Lee, D., Yoon, J., Kwon, O. and Lee, J. (2017), Differential pH-sensitive sensor with DC electrode-offset compensation. Electron. Lett., 53: 251-253. https://doi.org/10.1049/el.2016.3330 (Year: 2017).*

*Primary Examiner* — Yi-Shan Yang
*Assistant Examiner* — Kyle W. Kretzer
(74) *Attorney, Agent, or Firm* — Mintz Levin Cohn Ferris Glovsky and Popeo, P.C.

(57) ABSTRACT

An implantable biosensor may be placed subcutaneously to monitor the concentration of an analyte in a body fluid. The biosensor may include an electrochemical cell and an antenna. The components of the biosensor, including the electrochemical cell and the antenna, may be disposed on a same substrate. The electrochemical cell may include multiple electrodes for performing electrochemical measurements that include a first measurement of the analyte concentration in the body fluid, a second measurement of a background interference present in the body fluid, and a third measurement of a pH level within the body fluid. The antenna may receive, from a transceiver, radio frequency (RF) waves for wirelessly powering the implantable biosen- (Continued)

sor. The antenna may further transmit, back to the transceiver, a backscatter signal encoding a result of the electrochemical measurements.

11 Claims, 17 Drawing Sheets

(51) Int. Cl.
*A61B 5/05* (2021.01)
*A61B 5/1486* (2006.01)

(52) U.S. Cl.
CPC .......... *A61B 5/145* (2013.01); *A61B 5/14539* (2013.01); *A61B 5/14865* (2013.01)

(56) References Cited

U.S. PATENT DOCUMENTS

| | | | |
|---|---|---|---|
| 2004/0036626 A1* | 2/2004 | Chan | G06K 19/0717 |
| | | | 374/E1.004 |
| 2006/0030771 A1* | 2/2006 | Levine | A61B 5/14539 |
| | | | 600/424 |
| 2006/0094946 A1* | 5/2006 | Kellogg | A61B 5/681 |
| | | | 435/14 |
| 2012/0245444 A1* | 9/2012 | Otis | G01N 27/3272 |
| | | | 600/345 |
| 2013/0178721 A1* | 7/2013 | Bird | A61B 5/14539 |
| | | | 600/301 |
| 2013/0197333 A1* | 8/2013 | Petisce | A61B 5/4839 |
| | | | 600/347 |
| 2013/0211270 A1* | 8/2013 | St. Laurent | A61B 5/682 |
| | | | 600/595 |
| 2014/0163338 A1* | 6/2014 | Roesicke | A61B 5/0031 |
| | | | 600/309 |
| 2014/0213867 A1* | 7/2014 | Pletcher | A61B 5/0004 |
| | | | 600/347 |
| 2015/0222130 A1 | 8/2015 | Goma et al. | |
| 2015/0335285 A1* | 11/2015 | Poon | A61N 5/0601 |
| | | | 600/301 |
| 2016/0278638 A1* | 9/2016 | Schwartz | A61B 5/14546 |
| 2017/0020424 A1* | 1/2017 | Holweg | A61B 5/14539 |

* cited by examiner

Multi-Electrode Electrochemical Cell 130

IMPLANTABLE BIOSENSOR

RELATED APPLICATION

This application is a national phase entry of Patent Cooperation Treaty Application No. PCT/US2018/036537 filed Jun. 7, 2018, entitled "IMPLANTABLE BIOSENSOR," which claims the benefit of priority to U.S. Provisional Application No. 62/517,828 entitled "IMPLANTABLE BIOSENSOR," filed on Jun. 9, 2017, the disclosures of which are incorporated herein by reference in their entirety.

STATEMENT OF GOVERNMENT SPONSORED SUPPORT

This invention was made with government support under 1621825 awarded by the National Science Foundation. The government has certain rights in the invention.

TECHNICAL FIELD

The subject matter disclosed herein relates generally to biosensors and more specifically to an implantable biosensor for measuring the concentration of an analyte within body fluids.

BACKGROUND

A variety of pathological and/or physiological conditions may be detected based on the concentration of one or more analytes present in extracellular body fluids such as, for example, interstitial fluid, blood plasma, and/or the like. For example, alcohol intoxication may be detected by measuring the concentration of ethyl glucuronide (EtG), hydrogen peroxide ($H_2O_2$), and/or other byproducts of alcohol metabolism. Alternatively and/or additionally, diabetes patients may monitor the progress of the disease by tracking levels of blood glucose ($C_6H_{12}O_6$).

SUMMARY

An apparatus is provided for monitoring the concentration of an analyte within a body fluid. The apparatus may include an electrochemical cell and an antenna. The electrochemical cell may be configured to perform a plurality of electrochemical measurements. The plurality of electrochemical measurements may include a first measurement of an analyte concentration in the body fluid, a second measurement of a background interference present in the body fluid, and a third measurement of a pH level within the body fluid. The antenna may be configured to transmit, to a transceiver, a backscatter signal encoding a result of the plurality of electrochemical measurements. The electrochemical cell and the antenna may be disposed on a same substrate.

In some variations, one or more features disclosed herein including the following features can optionally be included in any feasible combination. The antenna may be further configured to detect one or more radio frequency waves output by the transceiver. The apparatus may be wirelessly powered by the one or more radio frequency waves.

In some variations, the electrochemical cell may include a reference electrode, a control electrode, and a plurality of working electrodes. The plurality of working electrodes may include a first electrode for measuring the analyte concentration, a second working electrode for measuring the background interference, and a third working electrode for measuring the pH level. The electrochemical cell may perform the plurality of electrochemical measurements by at least applying a voltage differential across the reference electrode and each of the plurality of working electrodes. The voltage differential may trigger a current flow between the control electrode and each of the plurality of working electrodes. The plurality of electrochemical measurements may be performed by at least measuring the current flow between the control electrode and each of the plurality of working electrodes.

In some variations, the apparatus may further include a potentiostat coupled with the electrochemical cell. The potentiostat may be configured to control an operation of the electrochemical cell. The potentiostat may include one or more working electrode voltage control loops for biasing the plurality of working electrodes.

In some variations, the apparatus may further include a current-to-frequency converter coupled with the potentiostat. The current-to-frequency converter may be configured to implement a current selection logic for selecting between copies of the current flow between the control electrode and each of the plurality of working electrodes. The copies of the current flow may be generated by the potentiostat. The current selection logic may enable the generation of the backscatter signal to exhibit a cyclical pattern. The cyclical pattern may include a first quantity of cycles corresponding to the pH level, a second quantity of cycles corresponding to the analyte concentration, and a third quantity of cycles corresponding to the background interference.

In some variations, the apparatus may further include a rectifier-backscatter coupled with the current-to-frequency converter and the antenna. The rectifier-backscatter may be configured to generate the backscatter signal by at least modifying, based on an output of the current-to-frequency controller, the one or more radio frequency signals to encode the result of the plurality of electrochemical measurements. The rectifier-backscatter may have a backscatter switch driven by the output of the current-to-frequency converter.

In some variations, the apparatus may further include a bandgap reference and a voltage regulator. The bandgap reference and the voltage regulator may be coupled with the rectifier and backscatter. The bandgap reference and the voltage regulator may be configured to smooth and/or attenuate glitches in an output of the rectifier-backscatter.

In some variations, the rectifier-backscatter, the potentiostat, the current-to-frequency converter, the bandgap reference, and the voltage regulator may be disposed on the same substrate as the antenna and the electrochemical cell.

In some variations, the antenna may be a coil antenna.

In some variations, the apparatus may be coupled with the transceiver via a high frequency radio frequency link in order to minimize a size of the antenna.

In some variations, the apparatus may be a subcutaneous implant that is placed subcutaneously by an injection.

In some variations, an actual analyte concentration may be determined by correcting, based on the second measurement and/or the third measurement, the first measurement.

An apparatus is provided for monitoring the concentration of an analyte in with a body fluid. The apparatus may include an antenna configured to output one or more radio frequency waves for wirelessly powering a biosensor. The biosensor may be placed subcutaneously. The antenna may be further configured to receive, from the biosensor, a backscatter signal encoding a result of a plurality of electrochemical measurements performed by the biosensor. The backscatter signal may be received in response to the one or more radio frequency waves. The plurality of electrochemical measurements may include a first measurement of an analyte concentration in a body fluid, a second measurement of a background interference present in the body fluid, and a third measurement of a pH level within the body fluid.

In some variations, one or more features disclosed herein including the following features can optionally be included in any feasible combination. The apparatus may further include at least one data processor and at least one memory. The at least one memory may store instructions that result in operations when executed by the at least one data processor. The operations may include determining an actual concentration of the analyte in the body fluid by at least correcting, based at least on the second measurement and/or the third measurement, the first measurement.

In some variations, the correction of the first measurement may include subtracting, from the analyte concentration, the background interference.

In some variations, the correction of the first measurement may include correcting, based on the pH level and Nernst equation, the analyte concentration.

In some variations, the backscatter signal may exhibit a cyclical pattern. The cyclical pattern may include a first quantity of cycles that correspond to the pH level, a second quantity of cycles that correspond to the analyte concentration, and a third quantity of cycles that correspond to the background interference.

A method is provided for monitoring the concentration of an analyte within body fluids. The method may include performing, by a biosensor placed subcutaneously, a plurality of electrochemical measurements. The plurality of electrochemical measurements may include a first measurement of an analyte concentration in a body fluid, a second measurement of a background interference present in the body fluid, and a third measurement of a pH level within the body fluid. A backscatter signal encoding a result of the plurality of electrochemical measurements may be transmitted to a transceiver.

In some variations, one or more features disclosed herein including the following features can optionally be included in any feasible combination. The biosensor may detect one or more radio frequency waves output by the transceivers. The biosensor may be wirelessly powered by the one or more radio frequency waves.

In some variations, a voltage differential may be applied across a reference electrode and each of a plurality of working electrodes comprising the biosensor. The voltage differential may trigger a current flow between a control electrode comprising the biosensor and each of the plurality of working electrodes. The current flow between the control electrode and each of the plurality of working electrodes may be measured.

In some variations, the backscatter signal may be generated by generating copies of the current flow between the control electrode and each of the plurality of working electrodes. The copies of the current flow may be converted into an output frequency. The one or more radio frequency signals output by the transceiver may be modified based at least on the output frequency.

In some variations, the backscatter signal may be generated to exhibit a cyclical pattern by at least selecting between the copies of the current flow. The cyclical pattern may include a first quantity of cycles that correspond to the pH level, a second quantity of cycles that correspond to the analyte concentration, and a third quantity of cycles that correspond to the background interference.

A method is provided for monitoring the concentration of an analyte within body fluids. The method may include outputting, by a transceiver, one or more radio frequency waves for wirelessly powering a biosensor. The biosensor may be placed subcutaneously. A backscatter signal may be received from the biosensor in response to the one or more radio frequency waves. The backscatter signal may encode a result of a plurality of electrochemical measurements performed by the biosensor, the plurality of electrochemical measurements including a first measurement of an analyte concentration in a body fluid, a second measurement of a background interference present in the body fluid, and a third measurement of a pH level within the body fluid. An actual concentration of the analyte in the body fluid may be determined by at least correcting, based at least on the second measurement and/or the third measurement, the first measurement.

In some variations, one or more features disclosed herein including the following features can optionally be included in any feasible combination. The correction of the first measurement may include subtracting, from the analyte concentration, the background interference.

In some variations, the correction of the first measurement may include correcting, based on the pH level and Nernst equation, the analyte concentration.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to an implantable biosensor for monitoring the concentration of an analyte within bodily fluids, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the subject matter disclosed herein. In the drawings.

When practical, similar reference numbers denote similar structures, features, or elements.

DETAILED DESCRIPTION

Figure 1A:
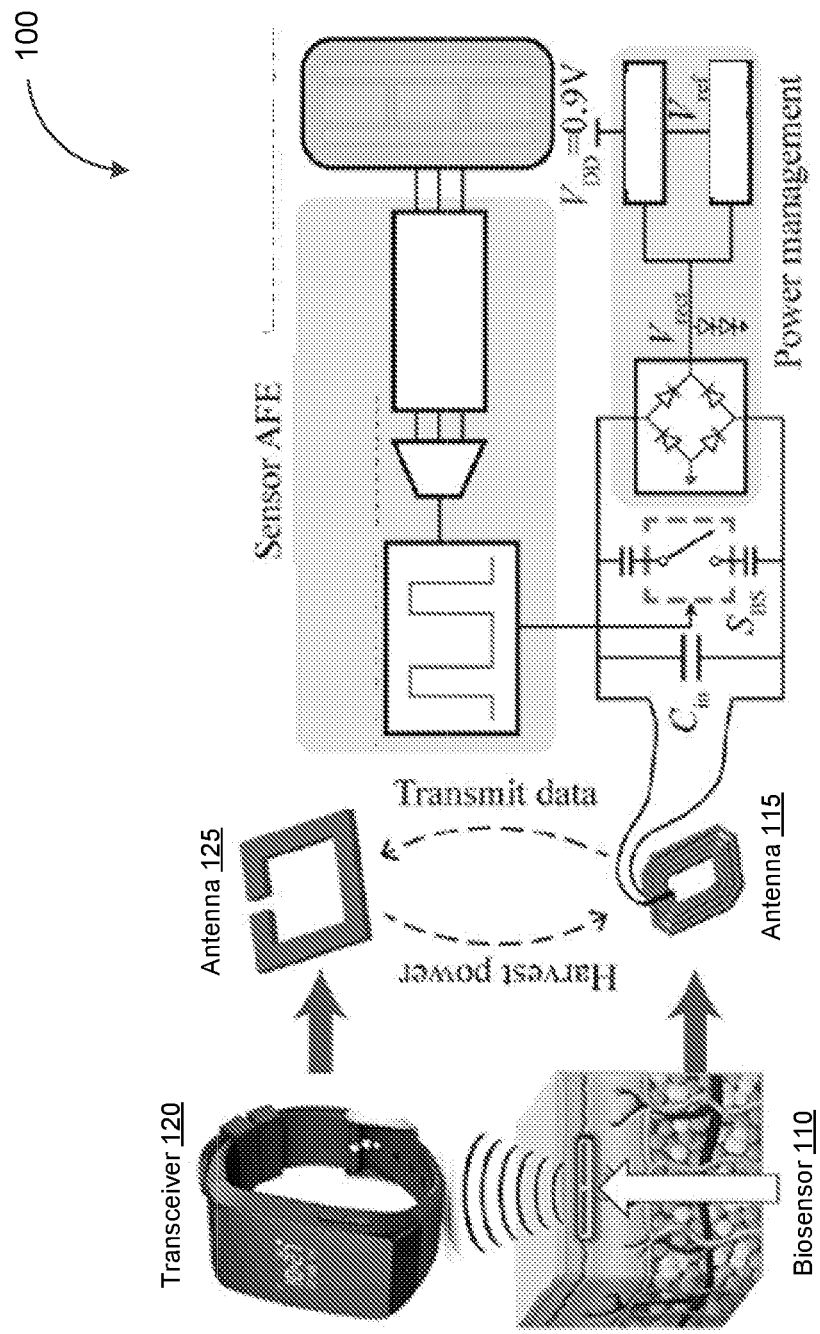
FIG. 1A depicts a system diagram illustrating a biosensor system, in accordance with some example embodiments.

Determining the concentration of one or more analytes present in extracellular body fluids may be vital for the detection, monitoring, and/or treatment of a variety of pathological and/or physiological conditions such as, for example, diabetes, substance intoxication, and/or the like. However, conventional techniques for measuring the concentration of analytes in body fluids may be complex, time-consuming, and inaccessible. Moreover, these conventional measurement techniques tend to be unsuitable for long term and/or continuous monitoring of analyte concentration. For example, a blood test to determine blood alcohol levels must take place in a laboratory and may take several hours to complete. As such, blood tests cannot be used to provide continuous and long term monitoring of blood alcohol levels, which may be essential in treating and/or preventing alcohol abuse.

In some example embodiments, an implantable biosensor may be placed subcutaneously to measure the concentration of an analyte in a body fluid such as, for example, blood plasma, interstitial fluid, and/or the like. The implantable biosensor may be capable of performing continuous and long term monitoring of the concentration of the analyte in the body fluid. For instance, the implantable biosensor may be configured to perform a plurality of electrochemical measurements that may be used to determine the concentration of the analyte (e.g., alcohol, narcotics, glucose, and/or the like) in a body fluid. According to some example embodiments, the implantable biosensor may be miniaturized by fully integrating all of the components of the implantable biosensor onto a single substrate (e.g., a 0.85× 1.5 mm$^2$ semiconductor chip and/or the like). In doing so, the implantable biosensor may be placed subcutaneously via minimally invasive techniques. For example, the implantable biosensor may be injected through a syringe.

In some example embodiments, the implantable biosensor may be coupled with an external transceiver configured to power the implantable biosensor wirelessly via a near-field electromagnetic coupling including, for example, inductive coupling, resonant inductive coupling, capacitive coupling, magnetodynamic coupling, optical coupling, and/or the like. As such, the external transceiver may wirelessly transfer power to the implantable sensor via one or more radio frequency (RF) signals. Wirelessly powering the implantable biosensor using an external power source instead of an onboard power source may enable a further miniaturization of the implantable biosensor. According to some example embodiments, the implantable biosensor may transmit, to the external transceiver, data that includes the results of the electrochemical measurements performed by the implantable biosensor. For example, the implantable biosensor may transmit data back to the external transceiver via backscattering. The external transceiver may determine, based on the data received from the implantable biosensor, the concentration of an analyte in a body fluid, thereby enabling the detection, monitoring, and/or treatment of one or more pathological and/or physiological conditions.

FIG. 1A depicts a system diagram illustrating a biosensor system 100, in accordance with some example embodiments. Referring to FIG. 1A, the biosensor system 100 may include a biosensor 110 and a transceiver 120. As shown in FIG. 1A, the biosensor 110 may be placed on the interior of a body (e.g., subcutaneously and/or the like), for example, within a body fluid, while the transceiver 120 may remain on the exterior of the body. For instance, the biosensor 110 may be disposed within an interstitial fluid (ISF) of a body, which may be the quasi-stationary extracellular fluid surrounding cells and containing nutrients, metabolites, waste, and/or the like.

In some example embodiments, the biosensor 110 may be configured to perform a plurality of electrochemical measurements of the body fluid including, for example, amperometric measurements, potentiometric measurements, and/or the like. For example, the biosensor 110 may perform electrochemical measurements that correspond to an analyte concentration, background interference, and pH level within the body fluid. The result of these electrochemical measurements may be used, for example, by the transceiver 120, to determine the concentration of an analyte within the body fluid.

In some example embodiments, the biosensor 110 may be miniaturized by fully integrating all of the components biosensor 110 onto a single substrate such as, for example, a 0.85×1.5 mm$^2$ semiconductor chip and/or the like. The biosensor 110 may be further miniaturized by obviating an onboard power source such as, for example, a battery and/or the like. Miniaturizing the biosensor 110 may at least enable the biosensor 110 to be placed subcutaneously using a minimally invasive technique such as, for example, an injection with a high gauge syringe (e.g., a 16-gauge syringe).

In some example embodiments, the biosensor 110 may be electromagnetically coupled with the transceiver 120, for example, via a first antenna 115 in the biosensor 110 and a second antenna 125 in the transceiver 120. For instance, the transceiver 120 may wirelessly power the biosensor 110 by at least outputting, via the second antenna 125, one or more radio frequency (RF) signals. Alternatively and/or additionally, the biosensor 110 may transmit, back to the transceiver 120, data that includes a result of the electrochemical measurements performed by the biosensor 110.

According to some example embodiments, the biosensor 110 may be a passive transmitter that is capable of operating without an onboard power source which, as noted, may enable a miniaturization of the biosensor 110. As such, the biosensor 110 may transmit data to the transceiver 120 via backscatter. For example, the first antenna 115 at the biosensor 110 may detect the one or more radio frequency (RF) signals output by the transceiver 120 and modify these radio frequency (RF) signals to encode the results of the electrochemical measurements performed by the biosensor 110. The first antenna 115 at the biosensor 110 may further transmit, via backscatter, the modified radio frequency (RF) signals back to the transceiver 120. In some example embodiments, the first antenna 115 and/or the second antenna 125 may be coupled via a high frequency radio frequency (RF) link (e.g., 985 megahertz (MHz) and/or the like) in order to minimize the size of the first antenna 115. Minimizing the size of the first antenna 115 may further miniaturize the biosensor 110.

In some example embodiments, the biosensor 110, for example, the first antenna 115, may output a backscatter signal having a cyclical pattern that corresponds to the different types of electrochemical measurements that are present in the signal. That is, each cycle within the backscatter signal may correspond to the result of an electrochemical measurement such as, for example, analyte concentration, background interference, pH level, and/or the like. For example, in some example embodiments, the backscatter signals may exhibit an 8-cycle pattern in which the first two cycles correspond to a pH level within the body fluid, the next four cycles correspond to an analyte concentration within the body fluid, and the last two cycles correspond to a background interference within the body fluid.

In some example embodiments, the transceiver 120 may be configured to determine the concentration of the analyte within the body fluid based at least on the results of the electrochemical measurements performed by the biosensor 110. The transceiver 120 may further output a value corresponding to the concentration of the analyte, for example, by displaying the value at the transceiver 120 and/or sending the value to another device. As shown in FIG. 1A, the transceiver 120 may be a wearable device such as, for example, a smartwatch and/or the like. However, it should be appreciated that the transceiver 120 may be any type of processor-based device capable of being electromagnetically coupled with the biosensor 110 including, for example, a smartphone, a tablet personal computer (PC), a laptop computer, and/or the like.

Figure 1B:
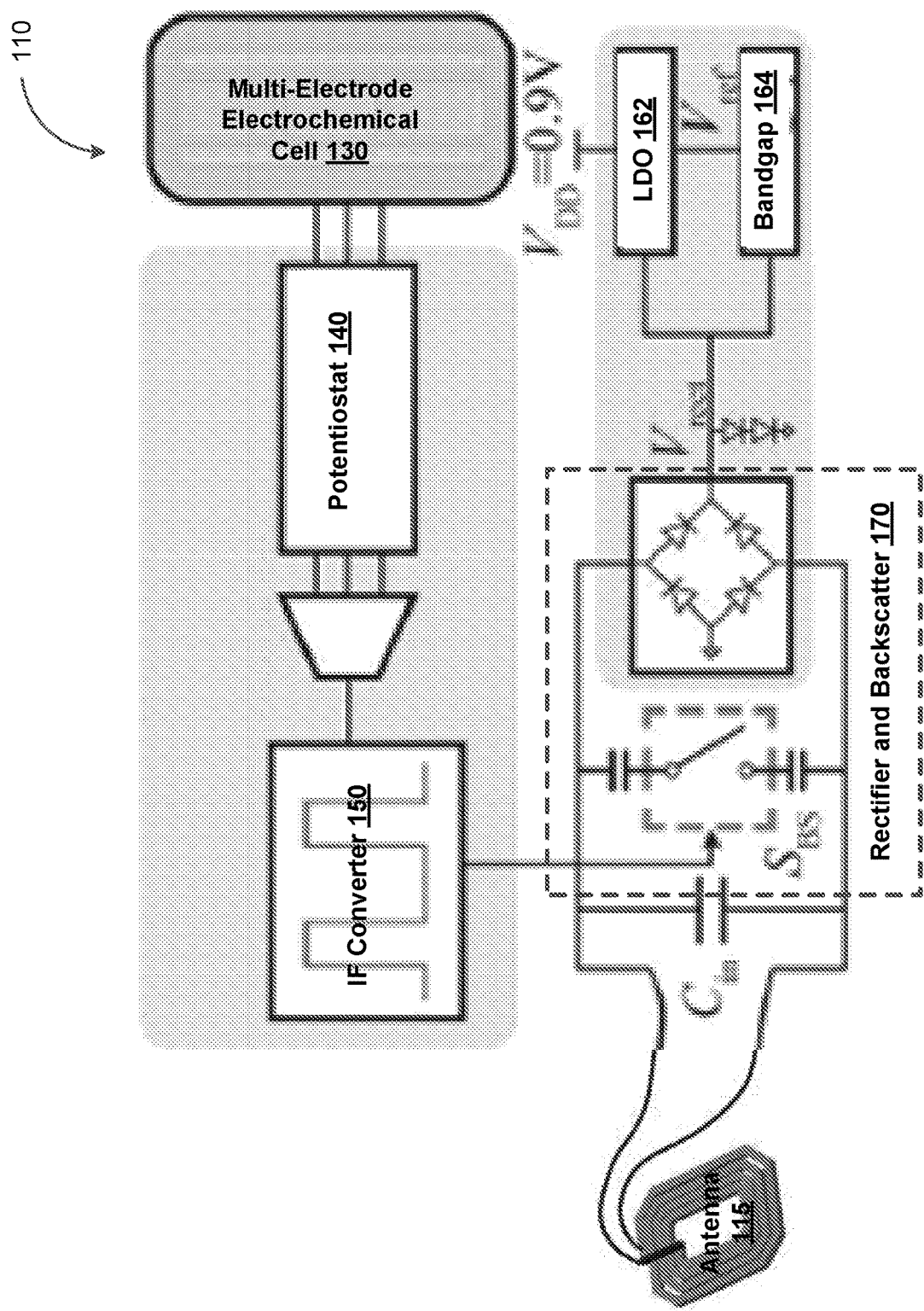
FIG. 1B depicts a schematic diagram illustrating a biosensor, in accordance with some example embodiments.

FIG. 1B depicts a schematic diagram illustrating the biosensor 110, in accordance with some example embodiments. As shown in FIG. 1B, the biosensor 110 may include a multi-electrode electrochemical cell 130, a potentiostat 140, a current-to-frequency (I-F) converter 150, a voltage regulator (LDO) 162, a bandgap 164, and a rectifier and backscatter 170. The biosensor 110 may further include the first antenna 115, which may be a coil antenna (e.g., a 4-turn coil having a quality factor Q of 10 and an inductance L of 40 nanohenries (nH)) and/or the like. It should be appreciated that the biosensor 110 may include different components than shown in FIG. 1B.

In some example embodiments, the biosensor 110 may be fully integrated such that all of the components of the biosensor 110 may be disposed on a single substrate such as, for example, a 0.85×1.5 mm² chip and/or the like. As such, the first antenna 115, the multi-electrode electrochemical cell 130, the potentiostat 140, the current-to-frequency (I-F) converter 150, the voltage regulator (LDO) 162, the bandgap 164, and the rectifier and backscatter 170 may all be disposed on the same substrate. Fully integrating the biosensor 110 in this manner may enable a miniaturization of the biosensor 110 such that the biosensor 110 may be placed subcutaneously using minimally invasive techniques such as, for example, injection and/or the like. Moreover, as noted, the biosensor 110 may lack an onboard power source, which may enable further miniaturization of the biosensor 110.

Figure 2A:
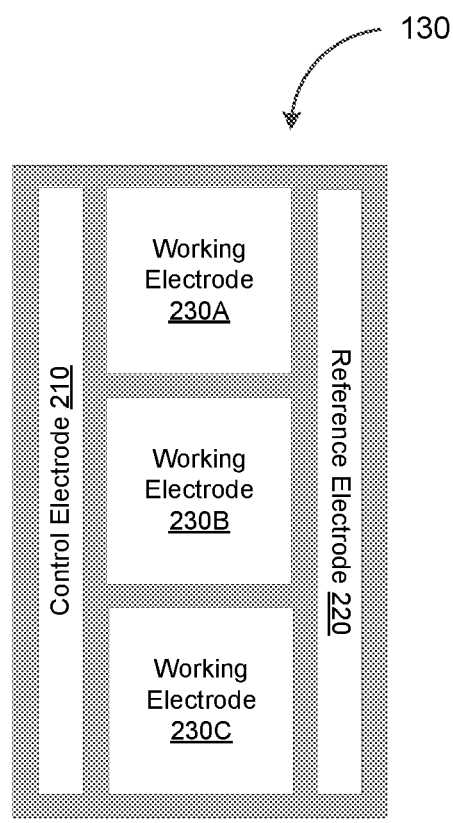
FIG. 2A depicts a block diagram illustrating a multi-electrode electrochemical cell, in accordance with some example embodiments.
Figure 2B:
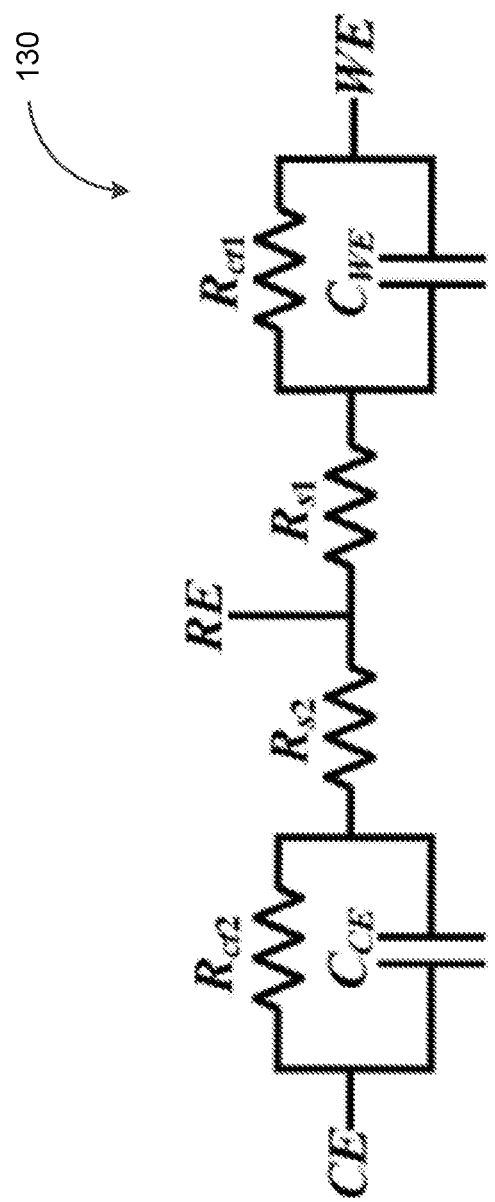
FIG. 2B depicts a schematic diagram illustrating a multi-electrode electrochemical cell, in accordance with some example embodiments.

FIG. 2A depicts a block diagram illustrating the multi-electrode electrochemical cell 130, in accordance with some example embodiments. FIG. 2B depicts a schematic diagram illustrating the multi-electrode electrochemical cell 130, in accordance with some example embodiments. Referring to FIGS. 1B and 2A-B, the multi-electrode electrochemical cell 130 may be part of the biosensor 110. As shown in FIGS. 2A-B, the multi-electrode electrochemical cell 130 may include a plurality of electrodes including, for example, a control electrode 210, a reference electrode 220, a first working electrode 230A, a second working electrode 230B, a third working electrode 230C, and/or the like. In some example embodiments, the control electrode 210, the reference electrode 220, the first working electrode 230A, the second working electrode 230B, and/or the third working electrode 230C may be each formed by depositing gold (Au) in openings on a metallic substrate such as, for example, aluminum (Al) and/or the like. The reference electrode 220 may further be covered with a silver (Ag) paste.

In some example embodiments, the multi-electrode electrochemical cell 130 may include multiple electrochemical sensors, each of which be capable of performing a specific type of electrochemical measurement to determine, for example, analyte concentration, background interference, pH levels, and/or the like. For example, as shown in FIG. 2A, the first working electrode 230A may be configured to measure analyte concentration, the second working electrode 230B may be configured to measure background interference, and the third working electrode 230C may be configured to measure pH levels.

The electrochemical measurements may be performed by at least applying a voltage differential (e.g., a 450 millivolt (mV) step) between the reference electrode 120 and each of the first working electrode 230A, the second working electrode 230B, and the third working electrode 230C, while measuring the resulting current flowing between each of the working electrodes and the control electrode 210. For example, the analyte concentration within the body fluid may be measured by at least applying a voltage differential between the reference electrode 220 and the third working electrode 230C while measuring the resulting current flow between the third working electrode 230C and the control electrode 210. Alternatively and/or additionally, the pH level within the body fluid may be measured by at least applying a voltage differential between the reference electrode 220 and the first working electrode 230A while measuring the resulting current flow between the first working electrode 230A and the control electrode 210. Meanwhile, the background interference present within the body fluid may be measured by at least applying a voltage differential between the reference electrode 220 and the second working electrode 230B while measuring the resulting current flow between the second working electrode 230B and the control electrode 210.

The current flow, for example, between the control electrode 210 and each of the first working electrode 230A, the second working electrode 230B, and/or the third working electrode 230C, may be determined based on the Cottrell equation, which is shown as Equation (1) below:

$$I_F(t) = \frac{nFAC_0\sqrt{D_0}}{\sqrt{\pi t}}, \tag{1}$$

wherein I-F may be the signal current, n may be quantity of electrons transferred per interaction, F may be the Faraday constant, A may be an area of the electrode, $C_O$ may be an initial concentration of a reducible analyte, $D_O$ may be a diffusion coefficient, and t may be time.

According to Equation (1), signal amplitude may be linearly dependent on the area of the electrode. However, the miniaturization of the biosensor 110 may require a minimization of the area of the control electrode 210, the reference electrode 220, the first working electrode 230A, the second working electrode 230B, and/or the third working electrode 230C. Minimizing the area of the control electrode 210, the reference electrode 220, the first working electrode 230A, the second working electrode 230B, and/or the third working electrode 230C may necessitate the inclusion of a low-noise potentiostat in the biosensor 110 such as, for example, the potentiostat 140.

Figure 2C:
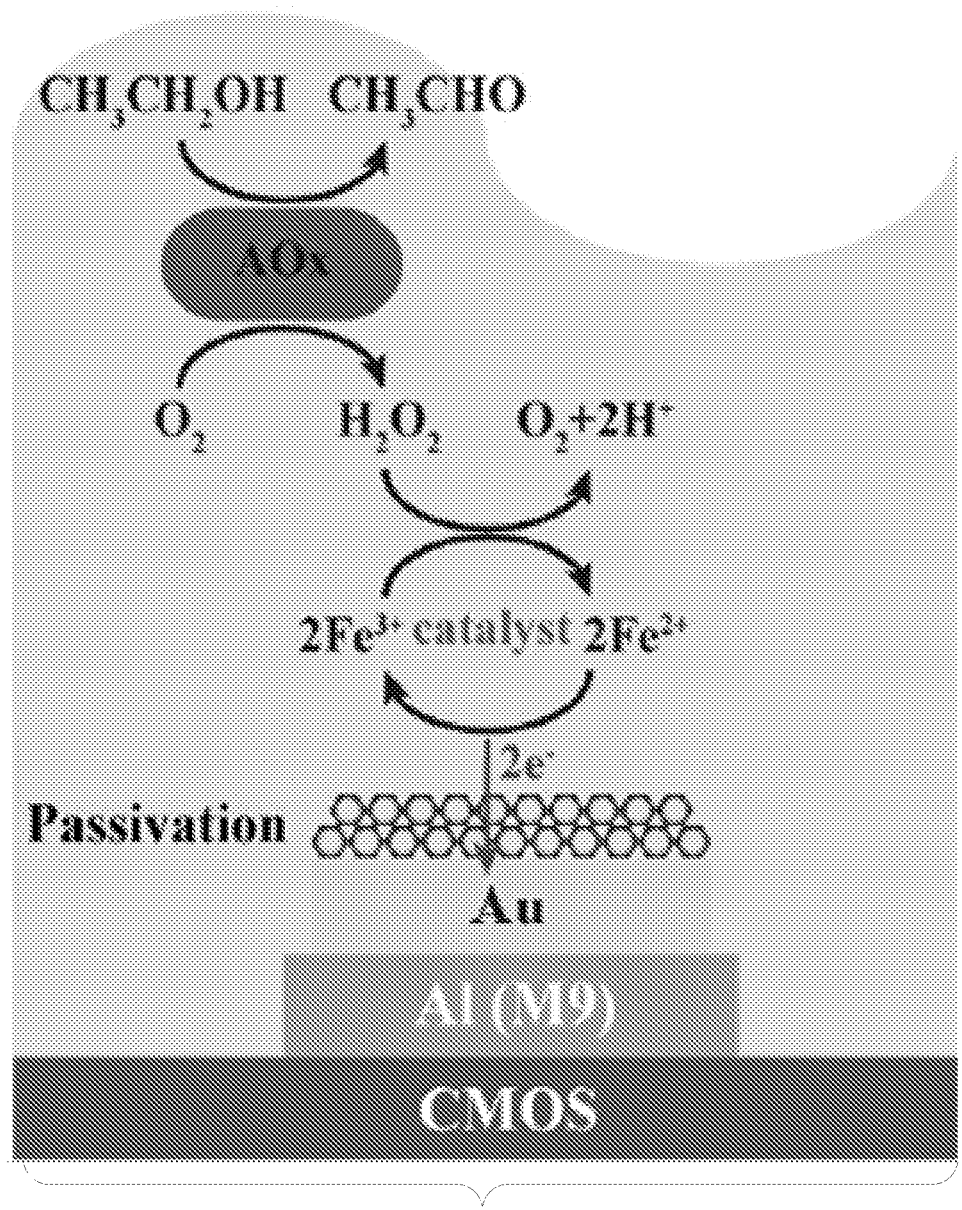
FIG. 2C depicts an enzymatic reaction associated with alcohol metabolism, in accordance with some example embodiments.

To further illustrate, the multi-electrode electrochemical cell 130 may be configured to perform electrochemical measurements that determine the concentration of the analyte ethanol present within a body fluid such as, for example, an interstitial fluid and/or the like. As shown in FIG. 2C, hydrogen peroxide ($H_2O_2$) may be a byproduct of an enzymatic reaction that occurs when alcohol oxidase (AOx) interacts with ethanol. The $H_2O_2$ byproduct may be further oxidized, for example, by iron oxide nanoparticles, to generate free electrons. These free electrons may be detected by the gold (Au) plating on the surface of the second working electrode 230B. In some example embodiments, the concentration of ethanol within interstitial fluids may exhibit a high correlation with blood alcohol levels. Accordingly, the results of the electrochemical measurements performed by the multi-electrode electrochemical cell 130 may be used to detect, monitor, and/or treat alcohol intoxication.

An electrochemical measurement of, for example, the concentration of ethanol in a body fluid, may be sensitive to environmental perturbations such as, for example, temperature drift, mechanical movements, pH variations, and/or the like. As such, in some example embodiments, the multi-electrode electrochemical cell 130 may perform additional electrochemical measurements, for example, of background interference and/or pH levels in the body fluid in order to correct for errors introduced by the environmental perturbations.

For example, in addition to measuring the concentration of ethanol present in the body fluid using the third working electrode 230C, the multi-electrode electrochemical cell 130 may include the first working electrode 230A for measuring pH levels in the body fluid. Alternatively and/or additionally, the multi-electrode electrochemical cell 130 may include the second working electrode 230B for measuring the background interference present in the body fluid, which may include a baseline concentration of ethanol and/or other interfering species already present in the body fluid. In some example embodiments, the background interference measured by the second working electrode 230B may be subtracted from the concentration of ethanol measured by the third working electrode 230C. Alternatively and/or additionally, the pH levels measured by the first working electrode 230A may be used to digitally correct, for example, based on the Nernst equation, the concentration of ethanol measured by the third working electrode 230C. The concentration of an analyte present in a body fluid may be pH dependent if the corresponding analyte reaction involves hydrogen ions ($H^+$) as in the case, for example, of the analyte ethanol. Accordingly, an independent pH measurement may enable the calculation of a formal potential $E^0$ and a retrospective digital correction of the analyte concentration measurement.

Figure 3:
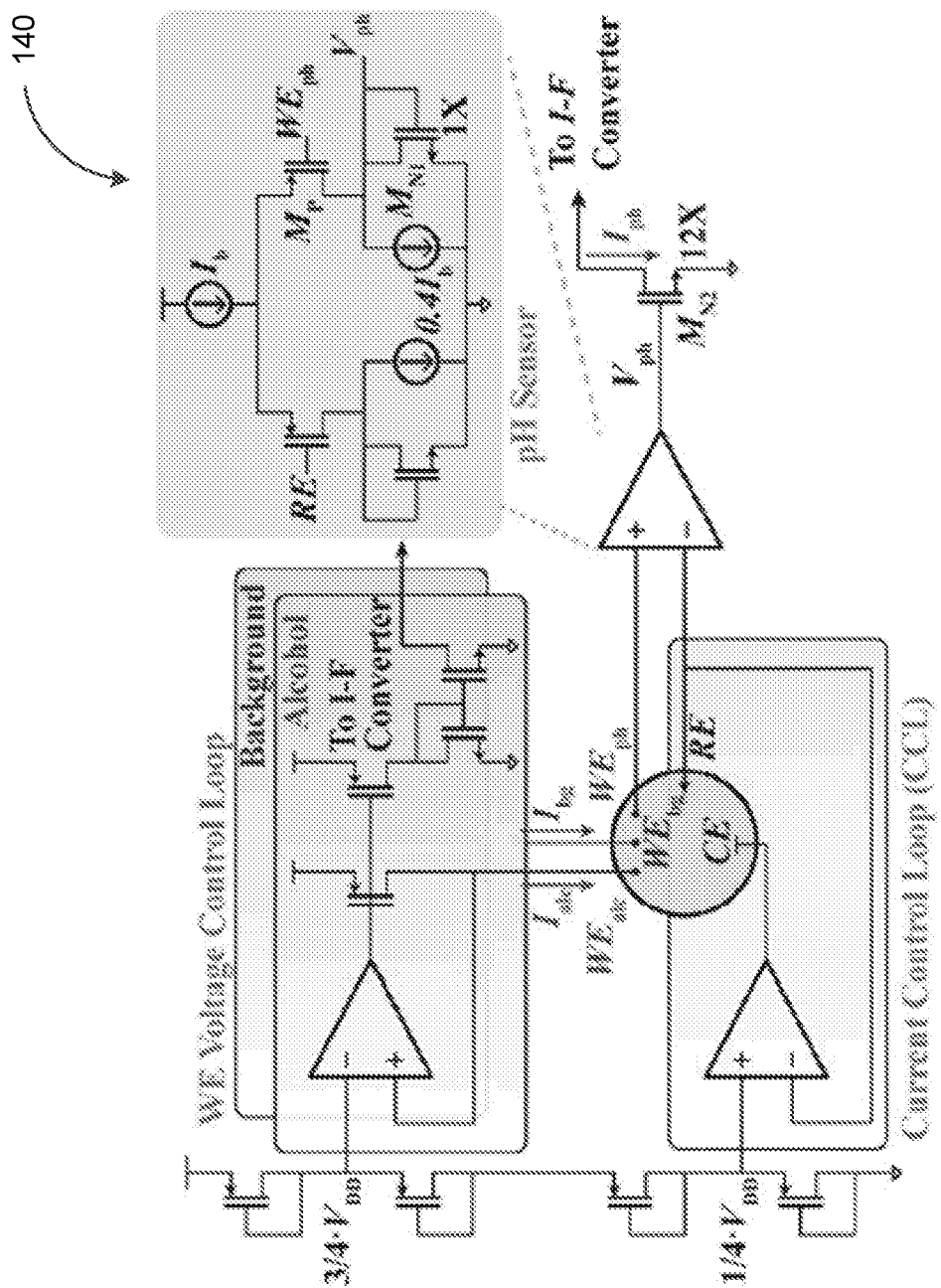
FIG. 3 depicts a schematic diagram illustrating a potentiostat, in accordance with some example embodiments.

FIG. 3 depicts a schematic diagram illustrating the potentiostat 140, in accordance with some example embodiments. Referring to FIGS. 1B and 3, the potentiostat 140 may be part of the biosensor 110 and may be configured to control the operations of the multi-electrode electrochemical cell 130 including, for example, the first working electrode 230A, the second working electrode 230B, and the third working electrode 230C. In some example embodiments, the potentiostat 140 may be a low-power multi-function potentiostat configured to support chronoamperometric measurements of the concentration of an analyte such as, for example, ethanol and/or the like. Alternatively and/or additionally, the potentiostat 140 may support potentiometric measurements of pH levels in the body fluid.

As shown in FIG. 3, the potentiostat 140 may include a working electrode (WE) voltage control loop configured to bias the working electrodes (e.g., the first working electrode 230A, the second working electrode 230B, and/or the third working electrode 230C) at $\frac{3}{4} \cdot V_{DD}$. The potentiostat 140 may further include a current mirror for generating copies of the current through the multi-electrode electrochemical cell 130 including, for example, the current flowing between the control electrode 210 and each of the first working electrode 230A, the second working electrode 230B, and/or the third working electrode 230C. Copies of the current through the multi-electrode electrochemical cell 130 may subsequently be converted, by the current-to-frequency (I-F) converter 150, into an output frequency usable to generate the backscatter signal. Although not shown in FIG. 3, a separate working electrode control loop may be required for readout from each of the second working electrode 230B (e.g., $WE_{bg}$) and the third working electrode 230C (e.g., $WE_{alc}$). Meanwhile, a shared current control loop (CCL) may bias the reference electrode 220 at $\frac{1}{4} \cdot V_{DD}$ to maintain a constant voltage differential (e.g., $\frac{1}{2} \cdot V_{DD}$) between the working electrodes and the reference electrode 220 where the enzymatic reaction occurs. For example, the signal currents $I_{alc}$ and $I_{bg}$ may flow from the third working electrode 230C (e.g., $WE_{alc}$) and the second working electrode 230B (e.g., $WE_{bg}$) to the control electrode 210 respectively, and may be limited by the current loop, which may set a maximum current (e.g., at 80 nanoamperes (nA)) in order to reduce unnecessary power consumption during start-up. The maximum current may be determined by the physiological levels of the analyte of interest. For instance, the physiological levels of ethanol may range from 2.17-43.4 mM, which may correspond to a blood alcohol level (BAC) of 0.01-0.2% and span the range from no behavioral impairment to loss of consciousness for a typical adult.

In some example embodiments, the potentiostat 140 may include a pH readout circuit. As shown in FIG. 3, the pH readout circuit may include a current starved diode connected differential transconductance amplifier. The amplifier may be sized to minimize an input-referred 1/f noise and have a high input impedance. A change in pH levels may induce a voltage at the first working electrode 220A (e.g., $WE_{pH}$) that may subsequently be converted to a current by the transconductance of the transistor $M_P$ (e.g., $g_{mp}$) and amplified (e.g., by twelvefold) from $M_{N2}$ to $M_{N3}$. A portion of the tail current (e.g., 80%) may be siphoned off to enable, for example, a fivefold reduction in power. Like the potentiostat 140, the overall transconductance (e.g., 1.2 microsiemens (μS)) may be matched to the physiological pH level range present in a body fluid such a body fluid such as, for example, interstitial fluid, and a full-scale range of the current-to-frequency converter 150 (e.g., 120 nanoamperes (nA)).

Figure 4:
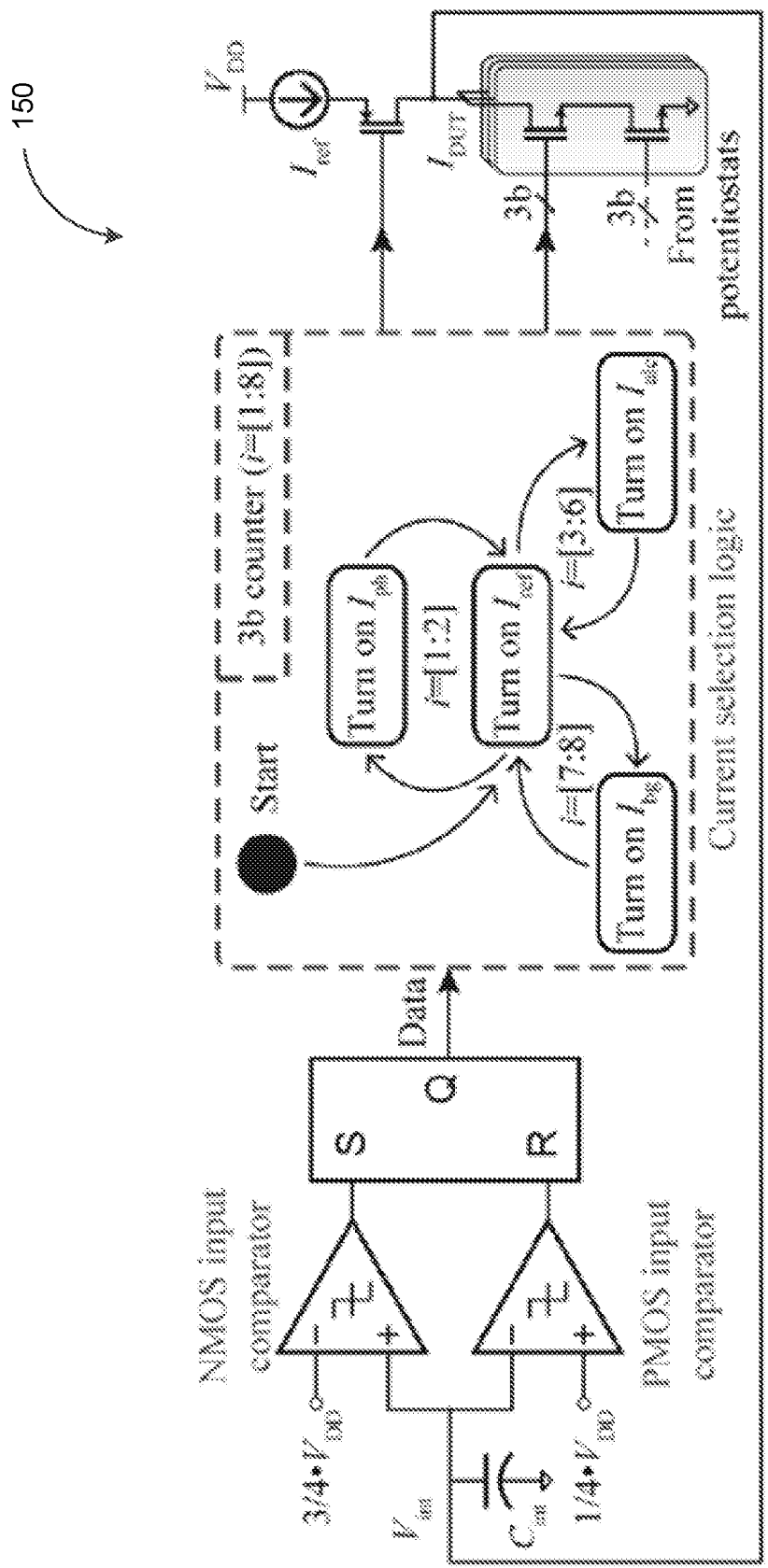
FIG. 4 depicts a schematic diagram illustrating an current-to-frequency (I-F) converter, in accordance with some example embodiments.

FIG. 4 depicts a schematic diagram illustrating the current-to-frequency (I-F) converter 150, in accordance with some example embodiments. Referring to FIGS. 1B and 4, the current-to-frequency converter 150 may be part of the biosensor 110. In some example embodiments, the current-to-frequency converter 150 may be configured to convert, into an output frequency, current from the multi-electrode electrochemical cell 130.

As shown in FIG. 4, current output by the potentiostat 140 may be mirrored to isolate the sensor from kickback. Furthermore, the current output by the potentiostat 140 may be injected into the current-to-frequency converter 150, which may be configured to translate the amplitude of the current into a frequency/duty cycle modulated waveform suitable for backscattering, for example, back to the transceiver 120. Digitization may performed on the transceiver 120 instead of the biosensor 110 in order to reduce the power consumption and form factor of the biosensor 110.

Figure 5:
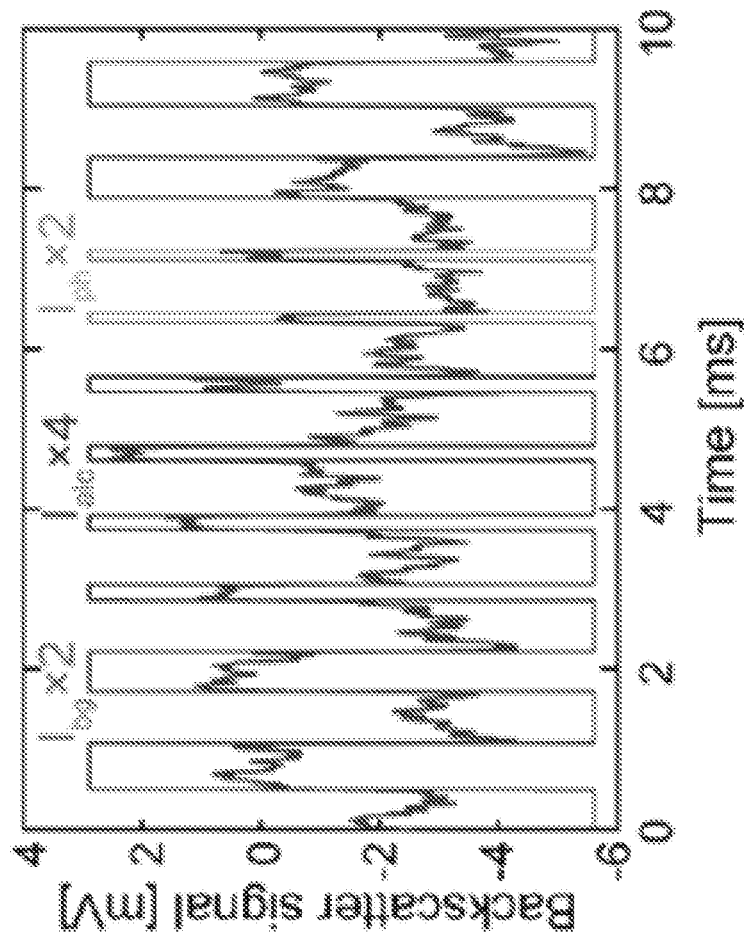
FIG. 5 depicts a graph illustrating a backscatter signal from a biosensor as a function of time, in accordance with some example embodiments.

In some example embodiments, the biosensor 110 may be configured to output a backscatter signal exhibiting a cyclical pattern. For example, as shown in FIG. 5, the backscatter signal that is transmitted by the biosensor 110 back to the transceiver 120 may exhibit an 8-cycle pattern in which the first two cycles correspond to a pH level measured by the first working electrode 230A (e.g., $WE_{ph}$), the next four cycles correspond to an analyte concentration measured by the third working electrode 230C (e.g., $WE_{alc}$), and the last two cycles correspond to a background interference measured by the second working electrode 230B (e.g., $WE_{bg}$). The cyclical pattern that is present within the backscatter signal from the biosensor 110 may obviate a need to synchronize clock cycles between the biosensor 110 and the transceiver 120.

In order to generate a backscatter signal having a cyclical pattern, the current-to-frequency converter 150 may implement a current selection logic to cycle through the current from each of the first working electrode 230A, the second working electrode 230B, and the third working electrode 230C. For instance, a reference current, $I_{ref}$ may charge a capacitor $C_{int}$ until a voltage $V_{int}$ exceeds a maximum threshold value (e.g., $\frac{3}{4} \cdot V_{DD}$), thereby triggering the n-type metal-oxide-semiconductor (NMOS) input comparator to flip the set-reset (SR) latch output. Next, one of the three sensor currents, $I_{DUT}$, may be selected to discharge $C_{int}$ until $V_{int}$ drops below a minimum threshold value (e.g., $\frac{1}{4} \cdot V_{DD}$). The duty cycle D and period T of the output from the current-to-frequency converter 150 may be determined, respectively, based on Equation (2) and Equation (3) below:

$$D = \frac{V_{DD} C_{int}}{2 I_{DUT}}, \quad (2)$$

$$T = \frac{V_{DD} C_{int}}{2 I_{ref}} \quad (3)$$

In accordance with Equations (2) and (3), $I_{DUT}$ may be obtained with respect to $I_{ref}$ by calculating the D/T ratio without first determining the values of $C_{int}$ or $V_{DD}$. To minimize efficiency loss due to backscatter operation, the value of $I_{ref}$ may be selected to be much less than $I_{DUT}$ (e.g., 5 nanoamperes (n)), thereby resulting in a duty cycle D of less than 20%. The comparator bandwidth may be greater than 50 kilohertz (kHz) in order to minimize error from comparator delay for the narrowest pulse width (e.g., 50 microseconds (μs)). Since there is no oscillator to clock the digital logic, a self-oscillating state-machine may sequentially cycle through the $I_{DUT}$ currents. A 3b divider driven by the output from the current-to-frequency converter 150 may divide the measurement period into an n quantity cycles (e.g., 8 cycles), in which $I_{alc}$ may be measured x times (e.g., four times), and $I_{bg}$ and $I_{ph}$ may each measured y times. The n-cycle measurement may repeat continuously in order to reduce the noise through averaging and provide a distinct signature to distinguish the three $I_{DUT}$'s at the receiver without any synchronization. Using custom subthreshold digital logic gates, the state-machine may consume minimal power (e.g., 300 picowatts (pW)).

Figure 6:
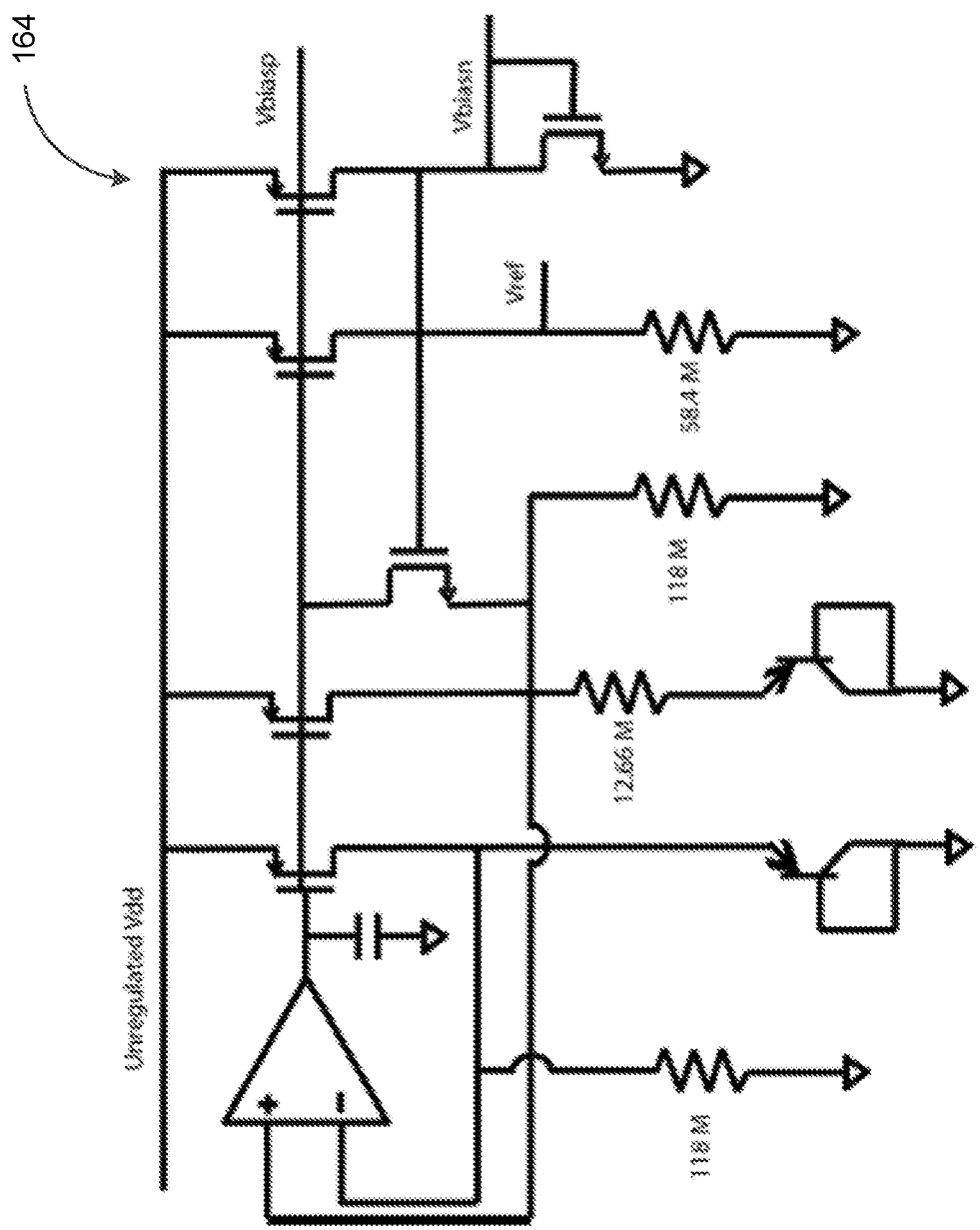
FIG. 6 depicts a schematic diagram illustrating a bandgap reference, in accordance with some example embodiments.
Figure 7:
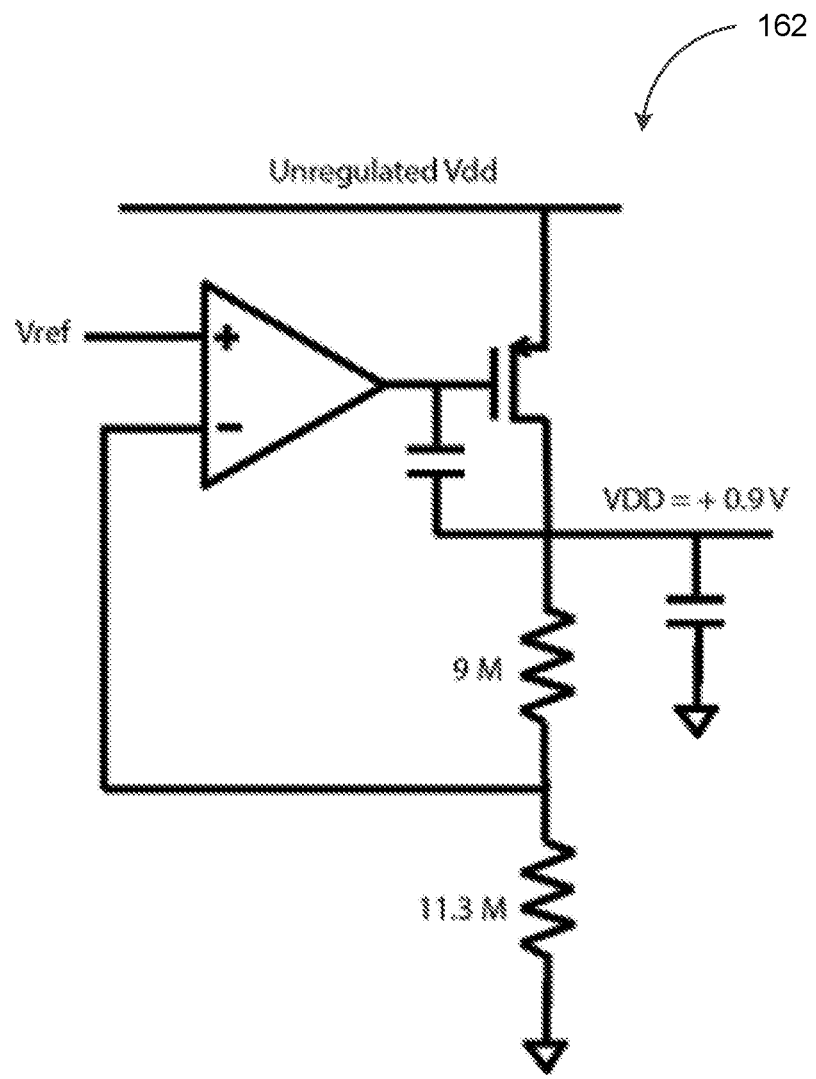
FIG. 7 depicts a schematic diagram illustrating a voltage regulator, in accordance with some example embodiments.

FIG. 6 depicts a schematic diagram illustrating the bandgap reference 162, in accordance with some example embodiments. FIG. 7 depicts a schematic diagram illustrating the voltage regulator 164, in accordance with some example embodiments. Referring to FIGS. 1B and 6-7, the bandgap reference 162 and the voltage regular 164 may generate a regulated supply voltage (e.g., 900 millivolts (mV)) and reference current (e.g., 5 nanoamperes (nA)).

Figure 8:
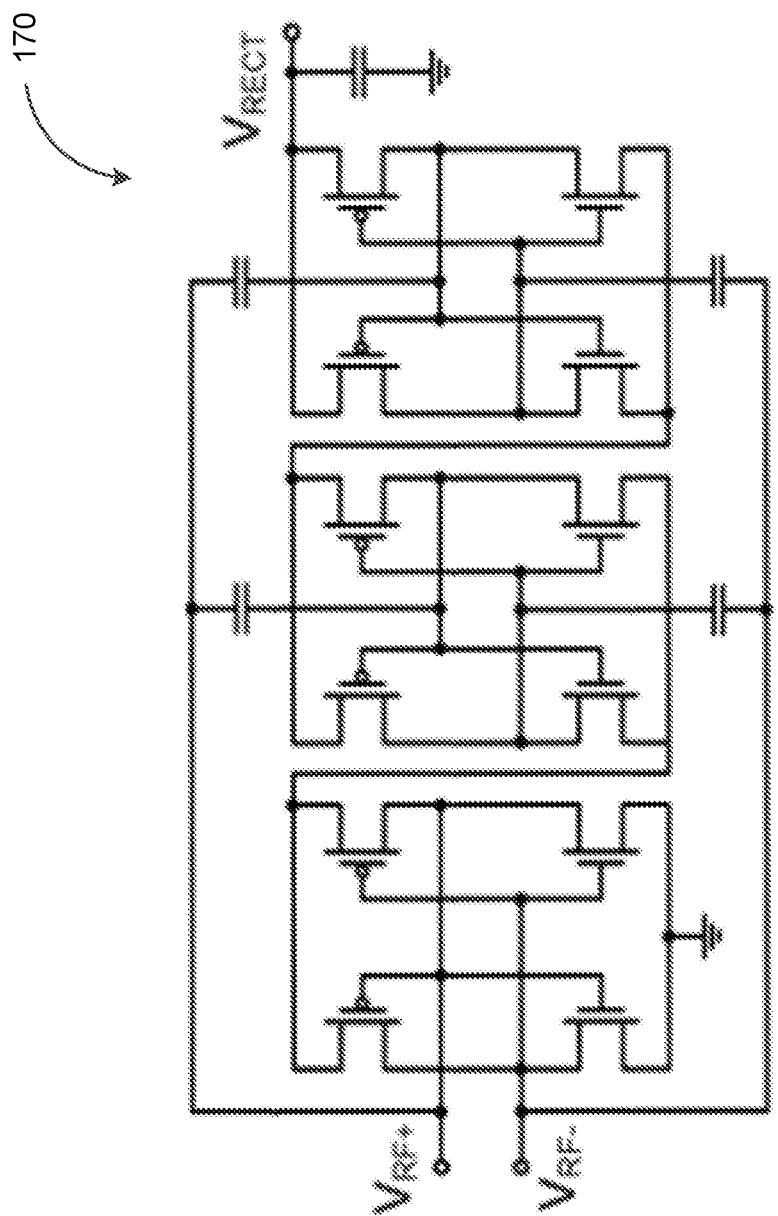
FIG. 8 depicts a schematic diagram illustrating a rectifier-backscatter, in accordance with some example embodiments.

FIG. 8 depicts a schematic diagram illustrating the rectifier-backscatter 170, in accordance with some example embodiments. Referring to FIGS. 1 and 8, the rectifier-backscatter 170 may be part of the biosensor 110. In some example embodiments, output from the current-to-frequency converter 150 may drive a backscatter switch $S_{BS}$ of the rectifier-backscatter 170. The backscatter switch $S_{BS}$ may modulate the rectifier input impedance and thus the output voltage of the transmitter. When $S_{BS}$ is on, two 1 picofarad (pF) metal-insulator-metal (MIM) capacitors may be connected in series, thereby causing the resonant frequency to shift down to ~800 megahertz (MHz). This downshift may translate into 0.4% carrier tone amplitude change at 10 mm separation that can be detected by the transmitter. Glitches in the output of the rectifier-backscatter 170 $V_{rect}$ caused by backscatter may be smoothed and attenuated by the voltage regulator 164. By moving the power burden of transmitting data from the biosensor 110 to the transceiver 120, the overall power consumption of the biosensor 110 may be minimized.

Figure 9:
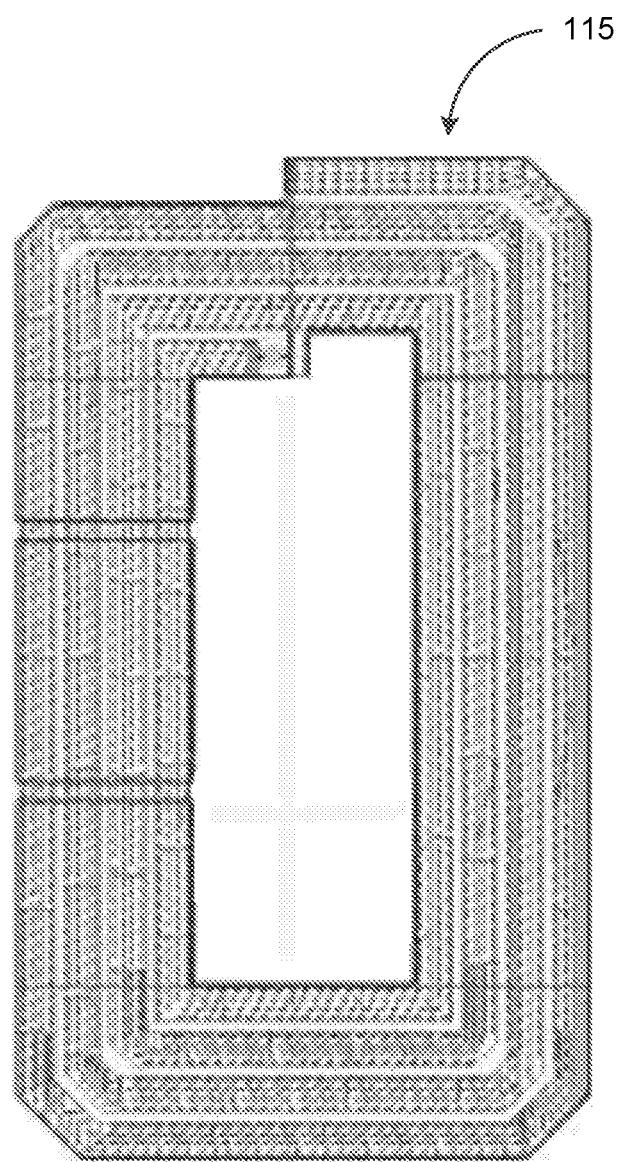
FIG. 9 depicts a plan view of an antenna, in accordance with some example embodiments.

FIG. 9 depicts a plan view of the first antenna 115, in accordance with some example embodiments. As shown in FIG. 1A, the first antenna 115 may be part of the biosensor 110. For instance, the first antenna 115 may be a fully integrated component of the biosensor 110 and may thus occupy a same substrate as the other components of the biosensor 110 including, for example, the multi-electrode electrochemical cell 130, the potentiostat 140, the current-to-frequency (I-F) converter 150, the voltage regulator (LDO) 162, the bandgap 164, and the rectifier and backscatter 170.

Referring to FIGS. 1A and 9, the first antenna 115 may be a coil antenna. For instance, as shown in FIG. 9, the first antenna 115 may be a four-turn coil antenna having a quality factor Q of 10 and an inductance L of 40 nanohenries (nH). Furthermore, the first antenna 115 may be configured to operate at a high frequency such as, for example, 985 megahertz (MHz) and/or the like. In some example embodiments, the frequency of first antenna 115 may be selected in order to minimize the size of the first antenna 115. However, it should be appreciated that the frequency of the first antenna 115 may also be selected based on biocompatibility as the radio frequency (RF) link between the first antenna 115 at the biosensor 110 and the second antenna 125 at the transceiver 125 traverses live tissue.

Figure 10A:
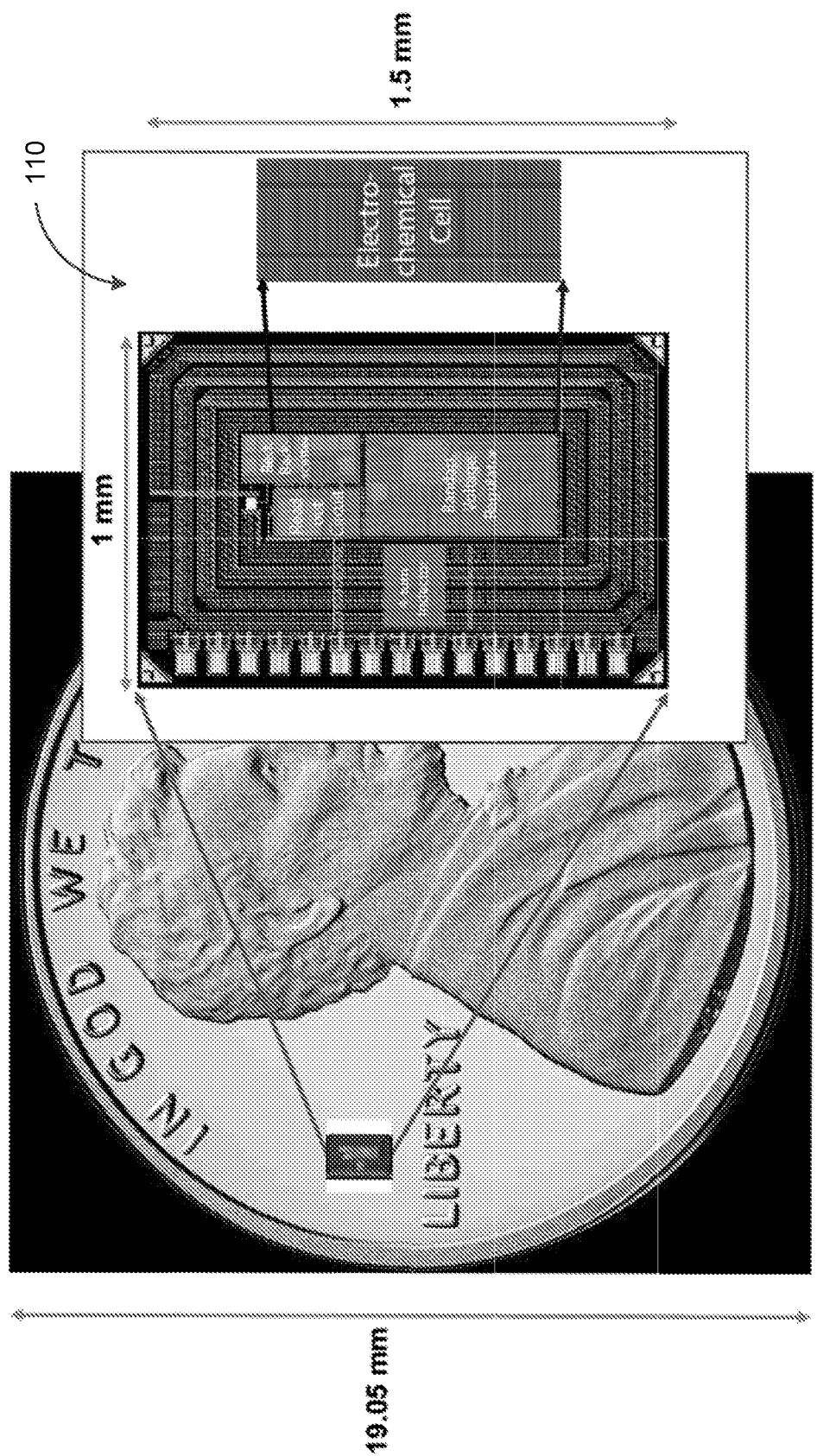
FIG. 10A depicts an implantable biosensor, in accordance with some example embodiments.
Figure 10B:
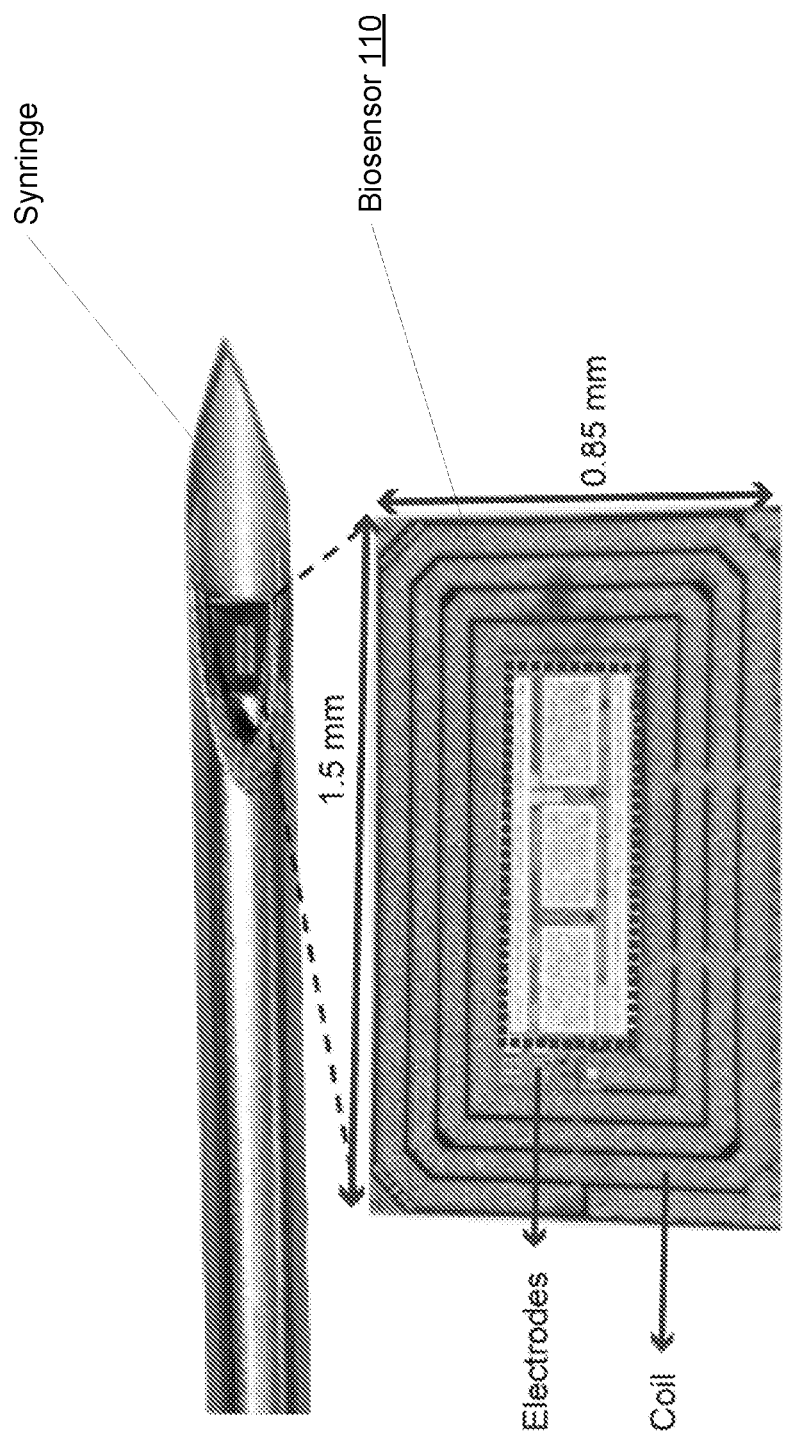
FIG. 10B depicts an implantable biosensor, in accordance with some example embodiments.

FIGS. 10A-B depict the biosensor 110, in accordance with some example embodiments. As noted, fully integrating the biosensor 110 and off boarding the power supply (e.g., to the transceiver 120) may enable a miniaturization of the biosensor 110. For example, all of the components of the biosensor 110 including, for example, the first antenna 115, the multi-electrode electrochemical cell 130, the potentiostat 140, the current-to-frequency (I-F) converter 150, the voltage regulator (LDO) 162, the bandgap 164, and the rectifier and backscatter 170 may all be disposed on a single substrate such as, for example, a 0.85×1.5 mm$^2$ chip and/or the like. Miniaturizing the biosensor 110 may enable the biosensor 110 to be placed subcutaneously using minimally invasive techniques such as, for example, an injection via a syringe. To further illustrate the miniaturized scale of the biosensor 110, FIG. 10A depicts the scale of the biosensor 110 relative to a penny while FIG. 10B depicts the scale of the biosensor 110 relative to a 16-gauge syringe.

Figure 11A:
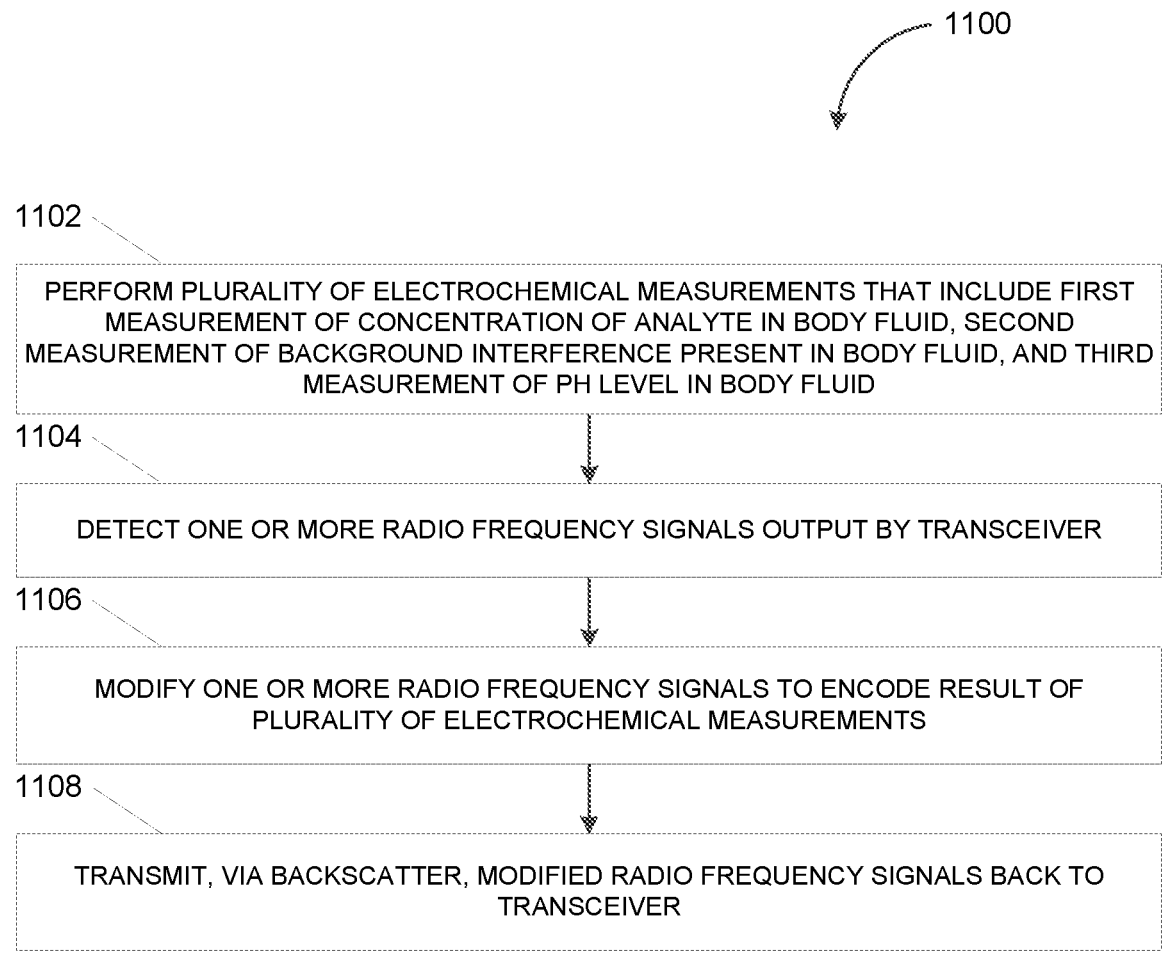
FIG. 11A depicts a flowchart illustrating a process for using an implantable biosensor to monitor the concentration of an analyte, in accordance with some example embodiments.

FIG. 11A depicts a flowchart illustrating a process 1100 for using an implantable biosensor to monitor the concentration of an analyte, in accordance with some example embodiments. Referring to FIGS. 1-11A, the process 1100 may be performed by the biosensor 110, for example, after the biosensor 110 has been placed subcutaneously. As noted, the miniaturized scale of the biosensor 110 may enable the biosensor 110 to be placed subcutaneously using minimally invasive techniques including, for example, an injection via a high-gauge syringe (e.g., a 16-gauge syringe) and/or the like.

At 1102, the biosensor 110 may perform a plurality of electrochemical measurements that include a first measurement of the concentration of an analyte in a body fluid, a second measurement of background interference present in the body fluid, and a third measurement of a pH level in the body fluid. In some example embodiments, the biosensor 110 may include the multi-electrode electrochemical cell 130, which may be configured to perform a variety of different types of electrochemical measurements. For example, the multi-electrode electrochemical cell 130 may include the first working electrode 230A for measuring the pH levels in a body fluid, the second working electrode 230B for measuring the background interference present in the body fluid, and the third working electrode 230C for measuring the concentration of an analyte in the body fluid. As noted, the multi-electrode electrochemical cell 130 may perform each electrochemical measurement by at least applying a voltage differential (e.g., a 450 millivolt (mV) step) across the reference electrode 220 and a corresponding working electrode while measuring the resulting current flow from the working electrode to the control electrode 210.

At 1104, the biosensor 110 may detect one or more radio frequency (RF) signals output by the transceiver 120. Furthermore, at 1106, the biosensor 110 may modify the one or more radio frequency (RF) signals to encode a result of the plurality of electrochemical measurements. At 1108, the biosensor 110 may transmit, via backscatter, the modified radio frequency (RF) signals back to the transceiver 120. In some example embodiments, the biosensor 110 may be a passive transmitter that is powered wirelessly by the transceiver 120. As shown in FIG. 1A, the transceiver 120 may wirelessly power the biosensor 110 by at least outputting one or more radio frequency (RF) signals. The biosensor 110, for example, the first antenna 115, may detect the radio frequency (RF) signals output by the transceiver 120. In order to transmit the results of the electrochemical measurements back to the transceiver 120, the biosensor 110 may modify the radio frequency (RF) signals from the transceiver 120 to encode the results of the electrochemical measurements. The modified radio frequency (RF) signals may be transmitted, via the first antenna 115, back to the transceiver 120 as a backscatter signal.

In some example embodiments, the biosensor 110, for example, the current-to-frequency converter 150, may generate the backscatter signal to exhibit a cyclical pattern. For instance, as shown in FIG. 5, the backscatter signal may exhibit an 8-cycle pattern in which the first two cycles correspond to a pH level measured by the first working electrode 230A (e.g., $WE_{ph}$), the next four cycles correspond to an analyte concentration measured by the third working electrode 230C (e.g., $WE_{alc}$), and the last two cycles correspond to a background interference measured by the second working electrode 230B (e.g., $WE_{bg}$). The cyclical pattern that is present within the backscatter signal from the biosensor 110 may obviate a need to synchronize clock cycles between the biosensor 110 and the transceiver 120.

Figure 11B:
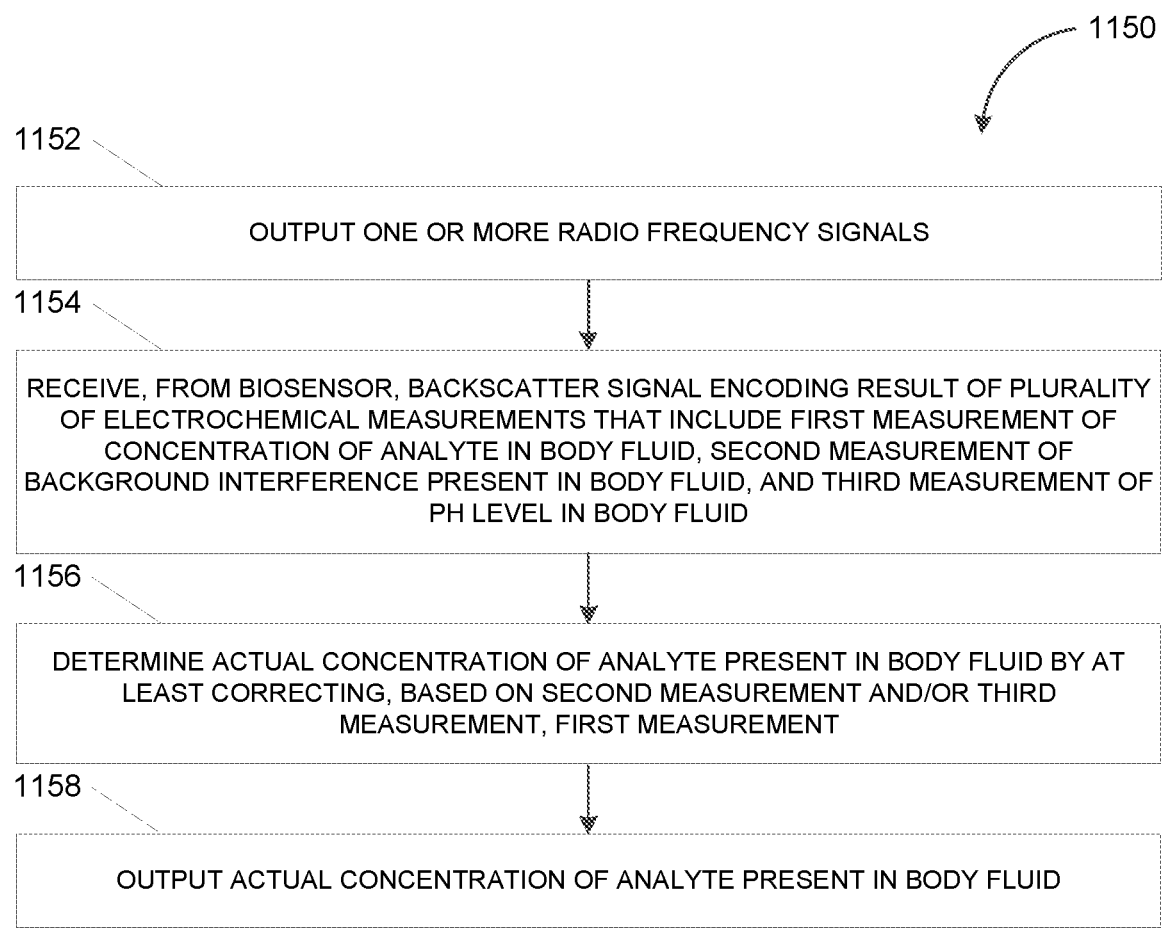
FIG. 11B depicts a flowchart illustrating a process for using an implantable biosensor to monitor the concentration of an analyte, in accordance with some example embodiments.

FIG. 11B depicts a flowchart illustrating a process 1150 for using an implantable biosensor to monitor the concentration of an analyte, in accordance with some example embodiments. Referring to FIGS. 1-10 and 11B, the process 1150 may be performed by the transceiver 120.

At 1152, the transceiver 120 may output one or more radio frequency (RF) signals. In some example embodiments, the miniature scale of the biosensor 110 may prevent the biosensor 110 from accommodating an onboard power source. Accordingly, the transceiver 120 may power the biosensor 110 wireless, for example, via a near-field electromagnetic coupling including, for example, inductive coupling, resonant inductive coupling, capacitive coupling, magnetodynamic coupling, and/or the like. As shown in FIG. 1A, the transceiver 120 may output, for example, via the second antenna 125, one or more radio frequency (RF) signals. These radio frequency (RF) signals may power the operations of the biosensor 110 including, for example, the performance of different electrochemical measurements and the generation of a backscatter signal that encodes the results of the electrochemical measurements.

At 1154, in response to the one or more radio frequency (RF) signals, the transceiver 120 may receive, from the biosensor 110, a backscatter signal encoding the result of a plurality of electrochemical measurements that include a first measurement of the concentration of an analyte in a body fluid, a second measurement of background interference present in the body fluid, and a third measurement of a pH level in the body fluid. For example, the transceiver 120 may receive, from the biosensor 110, a backscatter signal that encodes the results of the electrochemical measurements performed by each of the first working electrode 230A, the second working electrode 230B, and/or the third working electrode 230C. As noted, in some example embodiments, the backscatter signal from the biosensor 110 may exhibit a cyclic pattern. For instance, FIG. 5 shows a backscatter signal that exhibits an 8-cycle pattern in which the first two cycles correspond to a pH level measured by the first working electrode 230A (e.g., $WE_{ph}$), the next four cycles correspond to an analyte concentration measured by the third working electrode 230C (e.g., $WE_{alc}$), and the last two cycles correspond to a background interference measured by the second working electrode 230B (e.g., $WE_{bg}$).

At 1156, the transceiver 120 may determine an actual concentration of the analyte present in the body fluid by at least correcting, based at least on the second measurement and/or the third measurement, the first measurement. As noted, electrochemical measurements, for example, the measurement of analyte concentration in a body fluid, may be sensitive to environmental perturbations such as, for example, temperature drift, mechanical movements, pH variations, and/or the like. As such, in some example embodiments, the biosensor 110, for example, the multi-electrode electrochemical cell 130 may perform additional electrochemical measurements, for example, of background interference and/or pH levels in the body fluid in order to correct for errors introduced by the environmental perturbations.

For example, in addition to measuring the concentration of an analyte present in the body fluid using the third working electrode 230C, the biosensor 110, for example, the multi-electrode electrochemical cell 130 may include the first working electrode 230A for measuring pH levels in the body fluid and the second working electrode 230B for measuring the background interference present in the body fluid. In some example embodiments, to correct the analyte concentration measured by the third working electrode 230C, the transceiver 120 may subtract, from the analyte concentration, the background interference measured by the second working electrode 230B. Alternatively and/or additionally, the transceiver 120 may further digitally correct the analyte concentration measured by the third working electrode 230C based on the pH levels measured by the first working electrode 230A.

At 1158, the transceiver 120 may output the actual concentration of the analyte present in the body fluid. For example, in some example embodiments, upon determining the actual concentration of the analyte that is present in the body by at least correcting for the errors that may present in the results provided by the biosensor 110, the transceiver 120 may output the actual concentration of the analyte present in the body fluid by at least displaying one or more corresponding values. Alternatively and/or additionally, the transceiver 120 may output the actual analyte concentration by at least sending, to one or more other devices, the corresponding values.

Figure 12:
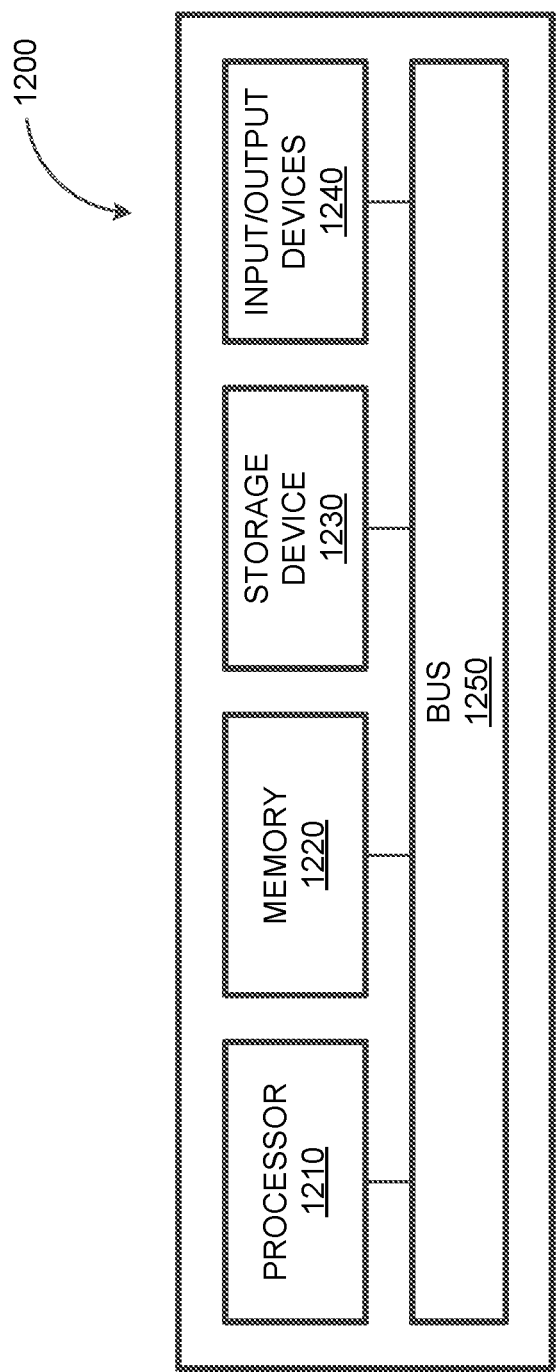
FIG. 12 depicts a block diagram illustrating a computing system consistent with implementations of the current subject matter.

FIG. 12 depicts a block diagram illustrating a computing system 1200 consistent with implementations of the current subject matter. Referring to FIGS. 1-12, the computing system 1200 can be used to implement the transceiver 120 and/or any components therein.

As shown in FIG. 12, the computing system 1200 can include a processor 1210, a memory 1220, a storage device 1230, and input/output devices 1240. The processor 1210, the memory 1220, the storage device 1230, and the input/output devices 1240 can be interconnected via a system bus 1250. The processor 1210 is capable of processing instructions for execution within the computing system 1200. Such executed instructions can implement one or more components of, for example, the transceiver 120. In some implementations of the current subject matter, the processor 1210 can be a single-threaded processor. Alternately, the processor 1210 can be a multi-threaded processor. The processor 1210 is capable of processing instructions stored in the memory 1220 and/or on the storage device 1230 to display graphical information for a user interface provided via the input/output device 1240.

The memory 1220 is a computer readable medium such as volatile or non-volatile that stores information within the computing system 1200. The memory 1220 can store data structures representing configuration object databases, for example. The storage device 1230 is capable of providing persistent storage for the computing system 1200. The storage device 1230 can be a floppy disk device, a hard disk device, an optical disk device, or a tape device, or other suitable persistent storage means. The input/output device 1240 provides input/output operations for the computing system 1200. In some implementations of the current subject matter, the input/output device 1240 includes a keyboard and/or pointing device. In various implementations, the input/output device 1240 includes a display unit for displaying graphical user interfaces.

According to some implementations of the current subject matter, the input/output device 1240 can provide input/output operations for a network device. For example, the input/output device 1240 can include Ethernet ports or other networking ports to communicate with one or more wired and/or wireless networks (e.g., a local area network (LAN), a wide area network (WAN), the Internet).

In some implementations of the current subject matter, the computing system 1200 can be used to execute various interactive computer software applications that can be used for organization, analysis and/or storage of data in various (e.g., tabular) format (e.g., Microsoft Excel®, and/or any other type of software). Alternatively, the computing system 1200 can be used to execute any type of software applications. These applications can be used to perform various functionalities, e.g., planning functionalities (e.g., generating, managing, editing of spreadsheet documents, word processing documents, and/or any other objects, etc.), computing functionalities, communications functionalities, etc. The applications can include various add-in functionalities or can be standalone computing products and/or functionalities. Upon activation within the applications, the functionalities can be used to generate the user interface provided via the input/output device 1240. The user interface can be generated and presented to a user by the computing system 1200 (e.g., on a computer screen monitor, etc.).

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively, or additionally, store such machine instructions in a transient manner, such as for example, as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive track pads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. An apparatus, comprising:
    an electrochemical cell comprising a reference electrode, a control electrode, a first working electrode, a second working electrode, and a third working electrode, the electrochemical cell configured to perform a plurality of electrochemical measurements, the plurality of electrochemical measurements including a first measurement of an analyte concentration in a body fluid, the first measurement corresponding to a first current flow between the first working electrode and the control electrode, a second measurement of a background interference present in the body fluid, the second measurement corresponding to a second current flow between the second working electrode and the control electrode, and a third measurement of a pH level within the body fluid, the third measurement corresponding to a voltage difference between the third working electrode and the reference electrode;
    a potentiostat coupled with the electrochemical cell, the potentiostat comprising at least a first current control loop configured to limit the first current flow between the first working electrode and the control electrode to a maximum current so as to reduce power consumption, wherein the maximum current is determined by a range of physiological levels of the analyte concentration present in the body fluid;
    a current-starved diode connected differential transconductance amplifier configured with an overall transconductance to match a physiological pH level range present in the body fluid; and
    an antenna configured to respond to one or more radio frequency waves output by a transceiver by at least transmitting, to the transceiver, a backscatter signal encoding a result of the plurality of electrochemical measurements, the backscatter signal exhibiting a cyclical pattern generated by selecting between the first current flow, the second current flow, and the voltage difference, the cyclical pattern including comprising a first quantity of cycles that correspond to the pH level, a second quantity of cycles that correspond to the analyte concentration, and a third quantity of cycles that correspond to the background interference, the apparatus being wirelessly powered by the one or more radio frequency waves instead of an onboard power source in order to minimize a first size of the apparatus, the one or more radio frequency waves having a high frequency such that the first size of the apparatus is further minimized by minimizing a second size of the antenna.

2. The apparatus of claim 1, further comprising:
    a current-to-frequency converter coupled with the potentiostat, wherein the current-to-frequency converter is configured to implement a current selection logic for selecting between copies of the first current flow, the second current flow, and the voltage difference.

3. The apparatus of claim 2, further comprising:
    a rectifier-backscatter coupled with the current-to-frequency converter and the antenna, the rectifier-backscatter configured to generate the backscatter signal by at least modifying, based on an output of the current-to-frequency converter, the one or more radio frequency waves to encode the result of the plurality of electrochemical measurements, the rectifier-backscatter having a backscatter switch driven by the output of the current-to-frequency converter.

4. The apparatus of claim 3, further comprising:
    a bandgap reference and a voltage regulator, the bandgap reference and the voltage regulator coupled with the rectifier-backscatter, and the bandgap reference and the voltage regulator configured to smooth and/or attenuate one or more supply glitches caused by the backscatter signal output by the rectifier-backscatter.

5. The apparatus of claim 4, wherein the rectifier-backscatter, the potentiostat, the current-to-frequency converter, the bandgap reference, and the voltage regulator are disposed on a same substrate as the antenna and/or the electrochemical cell.

6. The apparatus of claim 1, wherein the current-starved diode connected differential transconductance amplifier is further configured to siphon off a portion of a tail current to enable a reduction in power.

7. The apparatus of claim 1, wherein the apparatus is a subcutaneous implant.

8. The apparatus of claim 1, wherein the transceiver determines a corrected analyte concentration by correcting, based on the second measurement and/or the third measurement, the first measurement.

9. The apparatus of claim 1, wherein the electrochemical cell and the antenna are disposed on a same substrate.

10. A method comprising:

performing, by an electrochemical cell, a plurality of electrochemical measurements, the plurality of electrochemical measurements including a first measurement of an analyte concentration in a body fluid, the first measurement corresponding to a first current flow between a first working electrode and a control electrode, a second measurement of a background interference present in the body fluid, the second measurement corresponding to a second current flow between a second working electrode and the control electrode, and a third measurement of a pH level within the body fluid, and the third measurement corresponding to a voltage difference between a third working electrode and a reference electrode;

matching an overall transconductance of a current-starved diode connected differential transconductance amplifier with a physiological pH level range present in the body fluid; and limiting, by a current control loop of a potentiostat, the first current flow between the first working electrode and the control electrode to a maximum current so as to reduce power consumption, wherein the maximum current is determined by a range of physiological levels of the analyte concentration present in the body fluid.

11. The method as recited in claim 10, further comprising siphoning off a portion of a tail current of the current-starved diode connected differential transconductance amplifier to enable a reduction in power.

* * * * *